US007524510B2

(12) United States Patent
Arnold et al.

(10) Patent No.: US 7,524,510 B2
(45) Date of Patent: Apr. 28, 2009

(54) ALKYL-GLYCOSIDE ENHANCED VACCINATION

(75) Inventors: John Jefferson Arnold, Durham, NC (US); Chun-Ming Huang, Hoover, AL (US); Elias Meezan, Birmingham, AL (US); Dennis J. Pillion, Hoover, AL (US); De-Chu C. Tang, Hoover, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 11/360,761

(22) Filed: Feb. 23, 2006

(65) Prior Publication Data

US 2006/0233761 A1   Oct. 19, 2006

Related U.S. Application Data

(60) Provisional application No. 60/655,318, filed on Feb. 23, 2005.

(51) Int. Cl.
*A61K 31/70* (2006.01)
*A61K 39/00* (2006.01)
*A61K 45/00* (2006.01)

(52) U.S. Cl. .................. 424/278.1; 424/184.1; 514/24; 514/25; 514/42; 514/44

(58) Field of Classification Search ........................ None
See application file for complete search history.

(56) References Cited

U.S. PATENT DOCUMENTS

| 3,608,030 | A | 9/1971 | Tint |
| 3,837,340 | A | 9/1974 | Counter |
| 3,906,092 | A | 9/1975 | Hilleman et al. |
| 3,937,412 | A | 2/1976 | Damour |
| 3,950,512 | A | 4/1976 | Emery et al. |
| 3,962,424 | A | 6/1976 | Zygraich et al. |
| 4,089,801 | A | 5/1978 | Schneider |
| 4,217,344 | A | 8/1980 | Vanlerberghe et al. |
| 4,235,871 | A | 11/1980 | Papahadjopoulos et al. |
| 4,241,046 | A | 12/1980 | Papahadjopoulos et al. |
| 4,394,448 | A | 7/1983 | Szoka, Jr. et al. |
| 4,405,616 | A | 9/1983 | Rajadhyaksha |
| 4,557,934 | A | 12/1985 | Cooper |
| 4,594,244 | A | 6/1986 | Lehner et al. |
| 4,623,541 | A | 11/1986 | Elliot et al. |
| 4,623,544 | A | 11/1986 | Highnote |

(Continued)

FOREIGN PATENT DOCUMENTS

EP          286798       10/1988

(Continued)

OTHER PUBLICATIONS

Tang, et al. Vaccination onto bare skin. Nature. 1997;388:729-730.*

(Continued)

*Primary Examiner*—Bruce Campell
*Assistant Examiner*—Stuart W Snyder
(74) *Attorney, Agent, or Firm*—Fish & Richardson P.C.

(57) ABSTRACT

Described herein are methods for the noninvasive immunization of a subject that involve alkyl glycosides. Also described herein are compositions, kits, and devices for the noninvasive immunization of a subject.

42 Claims, 3 Drawing Sheets

U.S. PATENT DOCUMENTS

| | | | |
|---|---|---|---|
| 4,674,490 A | 6/1987 | Frankel et al. | |
| 4,738,846 A | 4/1988 | Rose et al. | |
| 4,775,630 A | 10/1988 | Tibbetts et al. | |
| 4,797,368 A | 1/1989 | Carter et al. | |
| 4,806,350 A | 2/1989 | Gerber | |
| 4,863,970 A | 9/1989 | Patel et al. | |
| 4,868,289 A | 9/1989 | Magnusson et al. | |
| 4,929,442 A | 5/1990 | Powell | |
| 4,944,942 A | 7/1990 | Brown et al. | |
| 5,023,252 A | 6/1991 | Hseih | |
| 5,139,941 A | 8/1992 | Muzyczka et al. | |
| 5,182,258 A | 1/1993 | Chiou | |
| 5,206,163 A | 4/1993 | Renard et al. | |
| 5,369,095 A | 11/1994 | Kee et al. | |
| 5,384,128 A | 1/1995 | Meezan | |
| 5,494,807 A | 2/1996 | Paoletti et al. | |
| 5,505,945 A | 4/1996 | Gristina et al. | |
| 5,530,102 A | 6/1996 | Gristina et al. | |
| 5,547,932 A | 8/1996 | Curiel et al. | |
| 5,552,309 A | 9/1996 | March | |
| 5,580,859 A | 12/1996 | Felgner et al. | |
| 5,585,362 A | 12/1996 | Wilson et al. | |
| 5,589,466 A | 12/1996 | Felgner et al. | |
| 5,591,439 A | 1/1997 | Plotkin et al. | |
| 5,593,972 A | 1/1997 | Weiner et al. | |
| 5,616,326 A | 4/1997 | Spibey | |
| 5,616,329 A | 4/1997 | Newman et al. | |
| 5,635,380 A | 6/1997 | Naftilan et al. | |
| 5,645,834 A | 7/1997 | Cockrum | |
| 5,648,096 A | 7/1997 | Gander et al. | |
| 5,658,785 A | 8/1997 | Johnson | |
| 5,661,130 A | 8/1997 | Meezan | |
| 5,662,098 A | 9/1997 | Yoshida | |
| 5,665,362 A | 9/1997 | Inglis et al. | |
| 5,670,488 A | 9/1997 | Gregory et al. | |
| 5,679,647 A | 10/1997 | Carson et al. | |
| 5,693,622 A | 12/1997 | Wolff et al. | |
| 5,698,202 A | 12/1997 | Ertl et al. | |
| 5,698,443 A | 12/1997 | Henderson et al. | |
| 5,700,470 A | 12/1997 | Saito et al. | |
| 5,700,680 A | 12/1997 | Newton et al. | |
| 5,700,910 A | 12/1997 | Metzger et al. | |
| 5,703,055 A | 12/1997 | Felgner et al. | |
| 5,705,151 A | 1/1998 | Dow et al. | |
| 5,707,618 A | 1/1998 | Armentano et al. | |
| 5,707,812 A | 1/1998 | Horn et al. | |
| 5,716,613 A | 2/1998 | Guber et al. | |
| 5,718,902 A | 2/1998 | Yilma et al. | |
| 5,731,172 A | 3/1998 | Saito et al. | |
| 5,731,181 A | 3/1998 | Kmiec | |
| 5,736,387 A | 4/1998 | Paul et al. | |
| 5,739,118 A | 4/1998 | Carrano et al. | |
| 5,753,263 A | 5/1998 | Lishko et al. | |
| 5,753,500 A | 5/1998 | Shenk et al. | |
| 5,756,086 A | 5/1998 | Mcclelland et al. | |
| 5,762,939 A | 6/1998 | Smith et al. | |
| 5,763,270 A | 6/1998 | Eastman et al. | |
| 5,766,599 A | 6/1998 | Paoletti et al. | |
| 5,770,442 A | 6/1998 | Wickham et al. | |
| 5,780,280 A | 7/1998 | Lebkowski et al. | |
| 5,780,448 A | 7/1998 | Davis | |
| 5,786,211 A | 7/1998 | Johnson | |
| 5,789,390 A | 8/1998 | Descamps et al. | |
| 5,792,462 A | 8/1998 | Johnston et al. | |
| 5,795,972 A | 8/1998 | Kmiec | |
| 5,804,566 A | 9/1998 | Carson et al. | |
| 5,817,492 A | 10/1998 | Saito et al. | |
| 5,817,637 A | 10/1998 | Weiner et al. | |
| 5,820,868 A | 10/1998 | Mittal et al. | |
| 5,824,538 A | 10/1998 | Branstrom et al. | |
| 5,824,544 A | 10/1998 | Armentano et al. | |
| 5,830,177 A | 11/1998 | Li et al. | |
| 5,830,463 A | 11/1998 | Duke et al. | |
| 5,830,730 A | 11/1998 | German et al. | |
| 5,830,877 A | 11/1998 | Carson et al. | |
| 5,834,256 A | 11/1998 | Finer et al. | |
| 5,846,559 A | 12/1998 | Hopp | |
| 5,849,719 A | 12/1998 | Carson et al. | |
| 5,851,806 A | 12/1998 | Kovesdi et al. | |
| 5,866,383 A | 2/1999 | Moss et al. | |
| 5,872,005 A | 2/1999 | Wang et al. | |
| 5,872,154 A | 2/1999 | Wilson et al. | |
| 5,874,279 A | 2/1999 | Cochran et al. | |
| 5,880,102 A | 3/1999 | George et al. | |
| 5,882,877 A | 3/1999 | Gregory et al. | |
| 5,885,808 A | 3/1999 | Spooner et al. | |
| 5,891,690 A | 4/1999 | Massie | |
| 5,952,008 A * | 9/1999 | Backstrom et al. | 424/499 |
| 5,998,382 A | 12/1999 | Furth et al. | |
| 6,087,341 A | 7/2000 | Khavari | |
| 6,100,614 A | 8/2000 | Lin | |
| 6,348,450 B1 | 2/2002 | Tang | |
| 6,632,456 B1 | 10/2003 | Backstrom | |
| 6,716,823 B1 | 4/2004 | Tang | |
| 6,808,922 B1 | 10/2004 | Bebbington et al. | |
| 2002/0169138 A1* | 11/2002 | Kunz et al. | 514/44 |
| 2003/0157113 A1* | 8/2003 | Terman | 424/184.1 |
| 2004/0028698 A1* | 2/2004 | Colau et al. | 424/202.1 |

FOREIGN PATENT DOCUMENTS

| | | |
|---|---|---|
| EP | 298142 | 1/1989 |
| EP | 406778 | 1/1991 |
| EP | 0638316 | 2/1995 |
| WO | WO 90/11092 | 10/1990 |
| WO | WO 92/11028 | 7/1992 |
| WO | WO 98/03641 | 1/1998 |
| WO | WO 99/08713 | 2/1999 |
| WO | WO 00/66179 | 11/2000 |

OTHER PUBLICATIONS

Zhu, et al. DNA Immunization of mice with a plasmid encoding Naisseria gonorrhea PorB protein by intramuscular injection and epidermal particle bombardment. Vaccine. 2004; 22:660-669.*

Berlo, et al. A prospective study in healthy volunteers of the topical absoption of a 5% rifaximin cream. Drugs Exp. Clin. Res. 1994; 20(5) Abstract only.*

Choi Y.H., et al., "Lactose-Poly(ethylene Glycol)-Grafted Poly-L-Lysine as Hepatoma Cell-Targeted Gene Carrier" Bioconjugate Chem 1998, vol. 9, p. 708-718.

Babiuk S. et al., "Cutaneous vaccination: the skin as an immunologically active tissue and the challenge of antigen delivery", J Controlled Release 2000, vol. 66, p. 199-214.

Alexander & Akhurst, et al., "Liposome-mediated Gene Transfer and Expression via the skin" Human Molecular Genetics 1995, vol. 4(12), p. 2279-2285.

Antohi, et al., "The Reactivity Pattern of Hemagglutinin-specific clonotypes from mice immunized as neonates or adults with naked DNA" International Immunology 1997, vol. 10(4), p. 663-668.

Autumn, et al. "Adhesive force of a single gecko foot-hair" Nature 2000, vol. 405(6787), p. 681-684.

Bramson, et al., "Enabling topical immunization via microporation: a novel method for pain-free and needle-free delivery of adenovirus-based vaccines" Gene Therapy 2003, vol. 10, p. 251-260.

Brandsma, et al., "Use of a rapid, efficient inoculation method to induce papillomas by cottontail rabbit papillomarvirus DNA shows that the *E7* gene is required" Proc. Natl. Acad. Sci. 1991, vol. 88, p. 4816-4820.

Brown, et al., "Adenoviral Vectors Given Intravaneously to Immunocomprised Mice Yield Stable Transduction of the Colonic Epithelium" Gastroenterology 1997, vol. 112, p. 1586-1594.

Carson, "Infectious Diseases in Day-Care Centers: Transmission and Approaches to Prevention" Drug Intell. Clin. Pharm. 1987, vol. 21(9), p. 694-701.

Chen, et al. "Characterization of an epibody. An antiidiotype that reacts with both the idiotype of rheumatoid factors (RF) and the antigen recognized by RF" J. of Exp. Med. 1985, vol. 161, p. 323-331.

Chen, et al., "Anti-hypervariable region antibody inducted by a defined peptide: An approach for studying the structural correlates of idiotypes" Proc. Natl. Acad. Sci. 1984, vol. 81, p. 1784-1788.

Chen, et al., "Characterization of Human Rheumatoid Factors With Seven Antiidiotypes Induced by Synthetic Hypervariable Region Peptides" J. Exp. Med. 1985, vol. 162, p. 487-500.

Chen, et al., "Delineation of a cross-reactive idiotype on human autoantibodies with antibody against a synthetic peptide", J. Exp. Med. 1984, vol. 159(5), p. 1502-1511.

Chiou, et al., "Improvement of Systemic Absorption of Insulin Through Eyes with Absorption Enhancers" J. of Pharm. Sci. 1989, vol. 78(10), p. 815-818.

Chiou, et al., Systemic Delivery of Insulin Through Eyes to Lower the Glucose Concentration, J. of Ocular Pharm. 1989, vol. 5(1), p. 81-91.

Choate and Khavari, "Direct Cutaneous Gene Delivery in a Human Genetic Skin Disease" Human Gene Therapy 1997, vol. 8, p. 1659-1665.

Ciernik, et al., "Puncture-Mediated Gene Transfer to the Skin" Human Gene Therapy 1996, vol. 7, p. 893-899.

Condon, et al., "DNA-based immunization by an vivo transfection of dendritic cells" Nat. Med. 1996, vol. 2(10), p. 1122-1128.

Corr, et al., "Costimulation provided by DNA immunization enhances antitumor immunity" J. Immunol. 1997, vol. 159(10), p. 4999-5004.

Corr, et al., "Gene Vaccination with Naked Plasmid DNA: Mechanism of CTL Priming" J. Exp. Med. 1996, vol. 184, p. 1555-1560.

Donnelly, et al., "DNA Vaccines" Life Sci. 1997, vol. 60(3), p. 163-172.

Fan, et al. "Immunization via hair follicles by topical application of naked DNA to normal skin" Nat. Biotech. 1999, vol. 17, p. 870-872.

Fong, et al. "The common occurrence of internal image type anti-idiotypic antibodies in rabbits immunized with monoclonal and polyclonal human IgM rheumatoid factors" Clin. Exp. Immunol. 1986, vol. 64(3): 570-80. (Abstract).

Glenn, et al., "Skin immunization made possible by cholera toxin" Nat. 1998, vol. 391(851), 1998.

Goldman, et al., "In vitro and in vivo gene delivery mediated by a synthetic polycationic amino polymer" Nat. Biotech. 1997, vol. 15(5), p. 462-466.

Goni, et al. "Sequence similarities and cross-idiotypic specificity of L chains among human monoclonal IgM kappa with anti-gamma-globulin activities" J. of Immunol. 1985, vol. 135(6): 4073-4079. (Abstract).

Gordon, et al., "Nasal absorption in insulin: Enhancement by hydrophobic bile salts" Pros. Natl. Acad. Sci. 1985, vol. 82, p. 7419-7423.

Gou, et al., "Efficient and sustained transgene expression in mature rat oligodendrocytes in primary culture" J of Neuroscience Res. 1996, vol. 43(1) p. 32-41.

Greenhalgh, et al., "Epidermis: An Attractive Target Tissue for Gene Therapy" Gene Therapy 1994, vol. 103(5), p. 63S-69S.

Heckert, et al., "A novel transcutaneous plasmid-dimethylsulfoxide delivery technique for avian nucleic acid immunization" Vet Immunol & Immunopath 2002, vol. 89, p. 67-81.

Hovgaard, et al., "Insulin Stabilization and GI Absorption" J. of Controlled Release 1999, vol. 19, p. 99-108.

Huyghe, et al., "Purification of a Type 5 Recombinant Adenovirus Encoding Human p53 by Column Chromatography" Human Gene Therapy 1995, vol. 6, p. 1403-1416.

Johnston et al., "The Use of Microparticle Injection to Introduce Genes Into Animal Cells In Vitro and In Vivo", Genetic Engineering 1993, vol. 15, p. 225-236.

Khavari, "Therapeutic gene delivery to the skin" Molecular Med. Today 1997, vol. 3(12), p. 533-538.

Krawczynski, et al., "Effect of immune globulin on the prevention of experimental hepatitis C virus infection" J. Infect. Dis. 1996, vol. 173(4): 822-828. (Abstract).

Krul, "Advances in Gene Therapy: Clear Progress Despite Setbacks" Therapy Markets and Emerging Technologies Spectrum Publ. 1996, Issue 112, p. 47. (Abstract).

Lee, et al., "Inhibition of IgE antibody formation by plasmid DNA immunization is mediated by both CD4+ and CD8+ T Cells" Int. Arch. Allergy Immunol. 1997, vol. 113(1-3), p. 227-230. (Abstract).

Lee, et al., "Control of immune responses by gene immunization" Ann. Med. 1998, vol. 30, p. 460-468.

Lee, et al., "Introduction of an Antigen-specific, CD1-restricted Cytotoxic T Lymphocyte Response In vivo" J. Exp. Med. 1998, vol. 187(3), p. 433-438.

Lees, et al., "Induction of protective immunity by topic application of a recombinant adenovirus expressing rabies virus glycoprotein" Vet. Micrbiol. 2002, vol. 85, p. 295-303.

Li, et al., "The feasibility of targeted selective gene therapy of the hair follicle" Nat. Med. 1995, vol. 1(7), p. 705-706.

Lu, et al., "A model for keratinocyte gene therapy: preclinical and therapeutic considerations" Proc. Assoc. Amer. Physicians 1996, vol. 108(2), 165-172.

Lu, et al., "Topical Application of Viral Vectors for Epidermal Gene Transfer" J. Invest. Dermatol. 1997, vol. 108, p. 803-808.

Mann and Hammarback, "Gene localization and developmental expression of light chain 3: a common subnuit of microtubule-associated protein 1A (MAP1A) and MAP1B" J. Neurosci. Res. 1996, vol. 43(5), p. 535-44. (Abstract).

McDonnell and Askari, "DNA Vaccines" NEJM 1996, vol. 334, p. 42-45.

Moses, et al., "Insulin Administered Intranasally as an Insulin-Bile Salt Aerosol-Effectiveness and Reproducibility in Normal and Diabetic Subjects" Diabetes 1983, vol. 32(11), p. 1040-147.

Murakami, et al., "Assessment of Enhancing Ability of Medium-Chain Alkyl Saccharides as New Absorption Enhancers in Rat Rectum" International J. of Pharm. 1992, 79, 159-169.

Niemiec, et al., "Perifollicular Transgenic Expression of Human Interleukin-1 Receptor Antagonist Protein Following Topical Application of Novel Liposome-Plasmid Formulations in Vivo" J. Pharm. Sci. 1997, vol. 86(6), p. 701-708.

Ogiso, et al. "Percutaneous Absorption of Elcatonin and Hypocalcemic Effect in Rat" Chem. Pharm. Bull. 1991, 39(2), p. 449-453.

Oshop, et al., "DNA vaccination in the avian" Vet. Immunol. & Immunopath. 2002, vol. 89(1), p. 1-12.

Panchagnula, et al., "Animal Models for Transdermal Drug Delivery" Meth. Find. Exp. Clin. Pharmacol. 1997, vol. 19(5), p. 335-341.

Paul, et al., "Transdermal immunization with large proteins by means of ultradeformable drug carriers" Eur. J. Immunol. 1995, vol. 25, p. 3521-3524.

Perkin-Elmer and Kimeragen "Perkin-Elmer and Kimeragen to develop novel gene repair molecules for treatment of genetic diseases" Norwalk, CT and Newtown, PA 1996.

Pillon, et al., "Systemic Absorption of Insulin Delivered Topically to the Rat Eye" Invest. Ophthalmol Vis. Sci. 1991, vol. 32(12), p. 3021-3027.

Prum, et al., "Hair, scales, fur, feathers of all the body coverings nature" Sci. Amer. 2003, p. 86-93.

Raz, et al., "Preferential induction of a $Th_1$ immune response and inhibition of specific IgE antibody formation by plasmid DNA immunization" Proc. Natl. Acad. Sci. 1996, vol. 93, p. 5141-5145.

Raz, et al., "Intradermal gene Immunication: The possible role of DNA uptake in the induction of cellular immunity to viruses" Proc. Natl. Acad. Sci. 1994, vol. 91, p. 9519-9523.

Remus, et al., "Insertion of Foreign DNA into an Established Mammalian Genome Can Alter the Methylation of Cellular DNA Sequences" J. of Virol. 1999, vol. 73(2), p. 1010-1022.

Rhodes, et al., "Autoantibodies in Infectious Mononucleosis Have Specificity For the Glycine-Alanine Repeating Region of the Epstein-Barr Virus Nuclear Antigen" J. Exp. Med. 1987, vol. 165, p. 1026-1040.

Saikh, et al., "Are DNA-based vaccines useful for protection against secreted bacterial toxins? Tetanus toxin test case" Vaccine 1998, vol. 16, p. 1029-1038.

Salzman, et al., "Intranasal Aerosolized Insulin" 1985, NEJM vol. 312(17), p. 1078-1084.

Sarphine, et al., "Bioavailability following transdermal powdered delivery (TPD) of radiolabeled insulin to hairless guinea pigs" J. Controlled Release 1997, vol. 47(1), p. 61-69.

Sato, et al., "Immunostimulatory DNA Sequences Necessary for Effective Intradermal Gene Immunization" Sci. 1996, vol. 273(5273), p. 352-354.

Scaria, et al. "Complementation of a human adenovirus early region 4 deletion mutant in 293 cells using adenovirus-polylysine-DNA complexes" Gene Ther. 1995, vol. 2(4), p. 295-298.

Scott, et al., "Abstracts for the "Congrès Annuel de Recherche Dermatologique 97" Sponsored by the "Société de Recherche Dermatologique" Faculté de Médicine de Tours—France, Apr. 10-11, 1997" J. Invest. Dermatol. 1997, vol. 108(5), p. 815-832.

Shi, et al., "DNA-based non-invasive vaccination onto the skin" Vaccine 1999, vol. 17, p. 2136-2141.

Shi, et al., "Protection against Tetanus by Needle-Free Inoculation of Adenovirus-Vectored Nasal and Epicutaneous Vaccines" J. Virol. 2001, vol. 75(23), p. 11474-11482.

Silverman, et al., "Structural characterization of the second major cross-reactive idiotype group of human rheumatoid factors. Association with the VH4 gene family" Arthritis Rheum. 1990, vol. 33(9), 1347-60. (Abstract).

Stephenson, "Defective adenoviruses as novel vaccines for the Flaviviridae" Clin Diag. Virol. 1998, vol. 10, p. 187-194.

Stephenson, "New Method to Repair Faulty Genes Stirs Interest in Chimeraplasty Technique" JAMA 1999, vol. 282(2), p. 119-121.

Tang, et al., "Vaccination onto bare skin" Nature 1997, vol. 388(6644), p. 729-730.

Tang, et al., "Butyrate-inducible and tumor-restricted gene expression by adenovirus vectors" Cancer Gene Therapy 1994, vol. 1(1), p. 15-20.

Tang, et al., "Genetic immunization is a simple method for eliciting an immune response" Nat. 1992, vol. 356(6365), p. 152-154.

Todryk, et al., "Induction of immune response to functional determinants of a cell surface streptococcal antigen" Immunol. 1996, vol. 87(1), p. 55-63.

Tsukui, et al., Transgenesis by adenovirus-mediated gene transfer into mouse zona-free eggs Nat. Biotech. 1996, vol. 14(8), p. 982-985.

Wang, et al., "Correction of a Deletion Mutant by Gene Targeting with an Adenovirus Vector" Molecular and Cellular Biol. 1993, vol. 13(2), p. 918-927.

Watanabe, et al., "Induction of antibodies to a kappa V region by gene immunization" J. of Immunol. 1993, vol. 151(5), p. 2871-2876 (Abstract).

Weiner, "Targeted follicular delivery of macromolecules via liposomes" Internl. J. of Pharm. 1998, vol. 162, p. 29-38.

Welch, et al., "Increased frequency of rheumatoid factor precursor B lymphyocytes after immunization of normal adults with tetanus toxoid" Clin. Exp. Immunol. 1983, vol. 51(2): 299-304. (Abstract).

Yamamoto, et al., "The Occular Route for Systemic Insulin Delivery in the Alino Rabbitt" J. of Pharm. and Exp. Therapeutics 1989, 249(1):249-255.

Yang, et al., "Gene gun and other non-viral approaches for cancer gene therapy" Nat. Med. 1995, vol. 1(5), p 481-481. (Abstract).

Yokoyama, et al, "DNA immunization: Effects of vehicle and route of administration on the induction of protective antiviral immunity" FEMS Immunol. and Med. Microb. 1996, vol. 14, p. 221-230.

Yu, et al., "Topical Gene Delivery to Murine Skin" The J. for Invest. Derm. 1999, vol. 112, p. 370-375.

Zhdanov, et al., "Nonviral methods of gene transfer in gene therapy" Vopr. Med. Khim. 1997, vol. 43(1), p. 3-12. (Abstract).

* cited by examiner

ALKYL-GLYCOSIDE ENHANCED VACCINATION

CROSS REFERENCE TO RELATED APPLICATIONS

This application claims the benefit of priority to U.S. Provisional Application No. 60/655,318, filed on Feb. 23, 2005, which is incorporated by reference herein in its entirety.

BACKGROUND

Activation of the immune system of vertebrates is an important mechanism for protecting animals against pathogens and malignant tumors. The immune system consists of many interacting components including the humoral and cellular branches. Humoral immunity involves antibodies that directly bind to antigens. Antibody molecules as the effectors of humoral immunity are secreted by B lymphocytes. Cellular immunity involves specialized cytotoxic T lymphocytes (CTLs), which recognize and kill other cells and produce non-self antigens. CTLs respond to degraded peptide fragments that appear on the surface of the target cell bound to MHC (major histocompatibility complex) class I molecules. It is understood that proteins produced within the cell are continually degraded to peptides as part of cellular metabolism. These fragments are bound to the MHC molecules and are transported to the cell surface. Thus the cellular immune system is constantly monitoring the spectra of proteins produced in all cells in the body and is poised to eliminate any cells producing non-self antigens.

Vaccination is the process of priming an animal for responding to an antigen. The antigen can be administered as a protein (classical) or as a gene, which then expresses the antigen (genetic immunization). The process involves T and B lymphocytes, other types of lymphoid cells, as well as specialized antigen presenting cells (APCs), which can process the antigen and display it in a form which can activate the immune system. Current modes for the administration of genetic vaccines have focused on invasive procedures, which include injection by needles, scarification, and gene gun-mediated penetration. Inoculation using invasive techniques requires equipment and personnel with special medical training, and is usually associated with discomfort and potential hazards (e.g., bleeding, infection).

The efficacy of a vaccine is measured by the extent of protection against a later challenge by a tumor or a pathogen. Effective vaccines are immunogens that can induce high titer and long-lasting protective immunity for targeted intervention against diseases after a minimum number of inoculations. For example, genetic immunization is an approach to elicit immune responses against specific proteins by expressing genes encoding the proteins in an animal's own cells. The substantial antigen amplification and immune stimulation resulting from prolonged antigen presentation in vivo can induce a solid immunity against the antigen. Genetic immunization simplifies the vaccination protocol to produce immune responses against particular proteins because the often difficult steps of protein purification and combination with adjuvant, both routinely required for vaccine development, are eliminated. Since genetic immunization does not require the isolation of proteins, it is especially valuable for proteins that may lose conformational epitopes when purified biochemically. Genetic vaccines may also be delivered in combination without eliciting interference or affecting efficacy, which may simplify the vaccination scheme against multiple antigens.

Noninvasive approaches to administering vaccines have been investigated. For example, topically-applied protein-based vaccines have been studied (Glenn et al., "Skin immunization made possible by cholera toxin," Nature 391:851, 1998); however, their usefulness is limited. The efficacy of genetic vaccines is in general superior to that of protein vaccines due to the de novo synthesis of antigens similar to natural infections (McDonnell and Askari, "DNA vaccines," New Engl J Med 334:42-45, 1996).

As described above, vaccination usually requires equipment, e.g., syringe needles or a gene gun, and special skill for the administration of the vaccine. There is a great need and desire in the art for the inoculation of vaccines by personnel without medical training and equipment. A large number of diseases could potentially be immunized against through the development of noninvasive vaccination because the procedure is simple, effective, economical, painless, and potentially safe. As a consequence, noninvasive vaccination may boost vaccine coverage in developing countries where medical resources are in short supply, as well as in developed countries due to patient comfort. Infectious diseases caused by (1) viruses, including AIDS and flu, (2) bacteria, including tetanus and TB, (3) parasites, including malaria, and (4) malignant tumors, including a wide variety of cancer types may all be prevented or treated with noninvasive vaccines without requiring special equipment and medical personnel. The compositions, devices, and methods described herein address this longstanding need.

SUMMARY

Described herein are methods for the noninvasive immunization of a subject. Also described herein are compositions, kits, and devices for the noninvasive immunization of a subject. The advantages of the invention will be set forth in part in the description which follows, and in part will be obvious from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying Figures, which are incorporated in and constitute a part of this specification, illustrate several aspects described below. Like numbers represent the same elements throughout the Figures.

DETAILED DESCRIPTION

Figure 1:
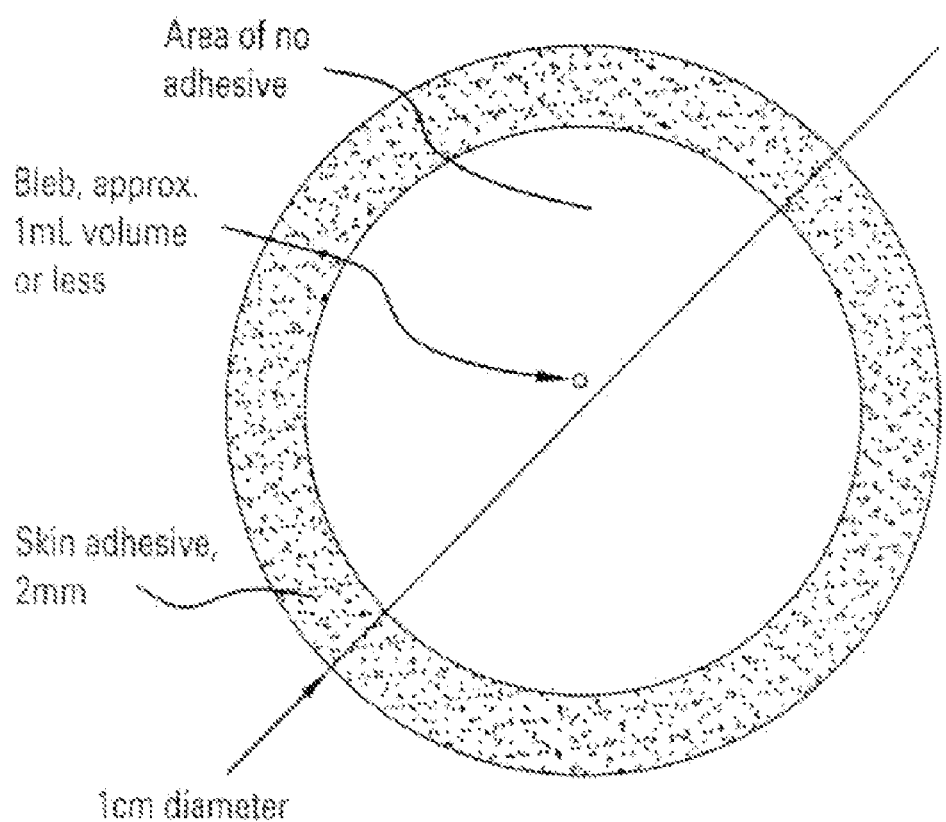
FIG. 1 shows a device for the administration of noninvasive vaccines.

Before the present compounds, compositions, kits, devices, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

It must be noted that, as used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

"Optional" or "optionally" means that the subsequently described event or circumstance can or cannot occur, and that the description includes instances where the event or circumstance occurs and instances where it does not. For example, the phrase "optionally substituted lower alkyl" means that the lower alkyl group can or can not be substituted and that the description includes both unsubstituted lower alkyl and lower alkyl where there is substitution.

Ranges may be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

Disclosed are compounds, compositions, and components that can be used for, can be used in conjunction with, can be used in preparation for, or are products of the disclosed methods and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a number of different alkyl glycosides and vaccines are disclosed and discussed, each and every combination and permutation of the alkyl glycoside and vaccine are specifically contemplated unless specifically indicated to the contrary. Thus, if a class of molecules A, B, and C are disclosed as well as a class of molecules D, E, and F and an example of a combination molecule, A-D is disclosed, then even if each is not individually recited, each is individually and collectively contemplated. Thus, in this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this disclosure including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

A. Compositions

As will be described below, the methods herein contemplate administering an alkyl glycoside and vaccine to a subject sequentially or concurrently. One way to administer the alkyl glycoside and vaccine concurrently is to admix the components together prior to administration. Depending upon the selection of the alkyl glycoside and the vaccine and mixture conditions, the alkyl glycoside and the vaccine may or may not react with one another. Described below are different aspects of the alkyl glycoside and vaccine that can be used herein.

1. Alkyl Glycoside

An alkyl glycoside is used in combination with a vaccine in order to immunize a subject. The term "alkyl group" as used herein is a branched or unbranched saturated hydrocarbon group of 1 to 25 carbon atoms, such as methyl, ethyl, n-propyl, isopropyl, n-butyl, isobutyl, t-butyl, pentyl, hexyl, heptyl, octyl, decyl, tetradecyl, hexadecyl, eicosyl, tetracosyl and the like. Examples of longer chain alkyl groups include, but are not limited to, an oleate group or a palmitate group. A "lower alkyl" group is an alkyl group containing from one to six carbon atoms.

The term alkyl is also used herein to include unsaturated hydrocarbons known as "alkenes" or "alkenyl groups," which as used herein refer to a hydrocarbon group of at least 2 carbon atoms with a structural formula containing at least one carbon-carbon double bond. Asymmetric structures such as $(AB)C=C(CD)$ are intended to include both the E and Z isomers (cis and trans).

The alkyl groups disclosed herein can also be substituted. As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For the purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. For example, the alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, sulfo-oxo, sulfonyl, sulfone, sulfoxide, or thiol.

In one aspect, the alkyl glycoside is any saccharide/carbohydrate joined by a linkage to any hydrophobic alkyl group. This includes, but is not limited to, alkyl groups bonded to the anomeric carbon of a saccharide/carbohydrate via an ether linkage as well as alkyl groups bonded to the anomeric carbon of a saccharide/carbohydrate through an ether linkage. Other linkages of alkyl groups and saccharide/carbohydrates are also possible, e.g., thioethers, thioesters, amines, amides, ureas, carbanates, and the like. The hydrophobic alkyl group can be chosen of any desired size, depending on the hydrophobicity desired and the hydrophilicity of the saccharide moiety. In one aspect, the alkyl group can be from 6 to 25 carbon atoms, 6 to 20 carbon atoms, 6 to 18 carbon atoms, 6 to 16 carbon atoms, or 6 to 14 carbon atoms. In other examples, the alkyl group can be 1, 2, 3, 4, 5, 6, 7, 8, 9, 10, 11, 12, 13, 14, 15, 16, 17, 18, 19, 20, 21, 22, 23, 24, or 25 group, where any of the stated values can form an upper or lower endpoint as appropriate. The term "saccharide" includes, but is not limited to, monosaccharides, oligosaccharides, or polysaccharides in straight chain or ring forms. Oligosaccharides are saccharides having two or more monosaccharide residues, while polysaccharides have more than two monosaccharide units.

The alkyl glycoside is generally nontoxic to the subject. "Nontoxic" as used herein, is defined as a molecule that has a sufficiently low toxicity to be suitable for administration to the subject. It is desirable that the alkyl glycoside be nonirritating to the tissue to which it is applied. The alkyl glycoside should be of minimal toxcity to the cell, such as not to cause damage to the cell. Toxicity for any given alkyl glycoside may vary with the concentration of alkyl glycoside used. It is also beneficial if the alkyl glycoside chosen is metabolized or eliminated by the body, and if this metabolism or elimination is done in a manner that will not be harmfully toxic. In one aspect, the alkyl glycoside can be nonionic.

The hydrophilic character of the alkyl glycoside can also vary, which can be quantified as the hydrophile-lipophile balance number. The term "hydrophile-lipophile balance number" (HLB) is a characteristic of individual surfactants that can be either calculated or determined empirically, as previously described (Schick, *Nonionic Surfactants*, Marcel Dekker, Inc., New York, p. 607, 1967). HLB can be calculated by the formula: 20×MW hydrophilic component/(MW hydrophobic component+MW hydrophilic component), where MW=molecular weight (Rosen, *Surfactants and Interfacial Phenomena*, John Wiley, New York, pp. 242-245, 1978). The HLB is a direct expression of the hydrophilic character of the surfactant, i.e., the larger the HLB, the more hydrophilic the compound. In one example, the alkyl glycoside has a hydrophile-lipophile balance number in the range of about 10 to 20, 11 to 19, 11 to 18, 11 to 17, 11 to 16, or 11 to 15. In other examples, the alkyl glycoside has a hydrophile-lipophile balance number of about 10, 11, 12, 13, 14, 15, 16, 17, 18, 19, or 20, where any of the stated values can form an upper or lower endpoint when appropriate.

In one example, the saccharide portion of the alkyl glycoside can be chosen from any currently commercially available saccharide species or can be synthesized. The saccharide can be a monosaccharide, a disaccharide, an oligosaccharide, a polysaccharide, or a combination thereof to form a saccharide chain. Examples saccharides useful herein include, but are not limited to, erythrose, threose, ribose, arabinose, xylose, lyxose, allose, altrose, glucose, mannose, gulose, idose, galactose, talose, fructose, maltose, cellobiose, maltotriose, maltotetraose, sucrose, lactose, trehalose, raffinose, or a derivative or combination thereof.

In other examples, one or more oxygen atoms within the saccharide can be substituted with sulfur in order to decrease susceptibility to hydrolytic cleavage by glycohydrolases in the body (Defaye and Gelas, in *Studies in Natural Product Chemistry*, Atta-ur-Rahman, ed., Elsevier, Amsterdam, Vol. 8, pp. 315-357, 1991). For example, the heteroatom of the sugar ring can be either oxygen or sulfur, or the linkage between monosaccharides in an oligosaccharide can be oxygen or sulfur (Horton and Wander, "Thio Sugars and Derivatives," *The Carbohydrates: Chemistry and Biochemistry*, Reyman and Horton eds., Academic Press, New York, 2d. Ed. Vol. IB, pp. 799-842, 1972). Oligosaccharides can have either the alpha or beta anomeric configuration (see Pacsu et al., in *Methods in Carbohydrate Chemistry*, Whistler et al., eds., Academic Press, New York, Vol. 2, pp. 376-385, 1963).

Many alkyl glycosides can be synthesized using techniques known in the art. For example, the techniques described in Rosevear et al., *Biochemistry* 19:4108-4115, 1980; Koeltzow and Urfer, *J Am Oil Chem Soc*, 61:1651-1655, 1984; U.S. Pat. Nos. 3,219,656; 3,839,318; Li et al., *J Biol Chem*, 266:10723-10726, 1991; or Gopalan et al., *J Biol Chem*, 267:9629-9638, 1992, which are incorporated by reference in their entireties, can be used to synthesize alkyl glycosides.

In yet other examples, the linkage between the hydrophobic alkyl group and the hydrophilic saccharide can include, but is not limited to, a glycosidic linkage, a thioglycosidic linkage (Horton), an amide linkage (Carbohydrates as Organic Raw Materials, Lichtenthaler ed., VCH Publishers, New York, 1991), an ureide linkage (Austrian Pat. 386,414 (1988); *Chem. Abstr.* 110:137536p, 1989, see Gruber and Greber, "Reactive Sucrose Derivatives" in *Carbohydrates as Organic Raw Materials*, Lichtenthaler, ed., VCH Publishers, New York, pp. 95-116, 1991), or an ester linkage (Sugar Esters: Preparation and Application, Colbert ed., Noyes Data Corp., New Jersey, 1974).

Examples of alkyl glycosides useful herein include, but are not limited to, hexyl-, heptyl-, octyl-, nonyl-, decyl-, undecyl-, dodecyl-, tridecyl-, tetradecyl, pentadecyl-, hexadecyl-, heptadecyl-, and octadecyl α- or β-D-malto side or -glucoside, which can be synthesized according to methods disclosed in, e.g., Koeltzow and Urfer, *J Am Oil Chem Soc*, 61:1651-1655, 1984, or obtained commercially from such suppliers as Anatrace Inc. (Maumee, Ohio), Calbiochem, (San Diego, Calif.), or Fluka Chemie, (Switzerland). Other examples of suitable alkyl glycoside include, but are not limited to, hexyl-, heptyl-, octyl-, nonyl-, decyl-, undecyl-, dodecyl-, tridecyl-, tetradecyl-, pentadecyl-, hexadecyl-, heptadecyl-, and octadecyl esters of sucrose. Further examples include alkyl thiomaltosides such as hexyl-, heptyl-, octyl-, dodecyl-, tridecyl-, and tetradecyl-β-D-thiomaltoside, which can be synthesized according to methods disclosed in Defaye and Pederson, "Hydrogen Fluoride, Solvent and Reagent for Carbohydrate Conversion Technology," in *Carbohydrates as Organic Raw Materials*, Lichtenthaler, ed., VCH Publishers, New York, 247-265, 1991, and Ferenci, *J Bacteriol* 144:7-11, 1980. Other suitable exampled include alkyl thioglucosides such as heptyl- or octyl-1-thio-α- or β-D-glucopyranoside, which are commercially available from such sources as Anatrace, Inc. (Maumee, Ohio) or can be synthesized by methods disclosed in, e.g., Saito and Tsuchiya, *Chem Pharm Bull,* 33:503-508, 1985. Yet further examples include alkyl thiosucroses, which can be synthesized according to methods disclosed in, e.g., Binder and Robyt, *Carbohydr Res,* 140:9-20, 1985, and alkyl maltotriosides, which can be synthesized according to methods disclosed in, e.g., Koeltzow and Urfer, *J Am Oil Chem Soc,* 61:1651-1655, 1984. Long chain aliphatic carbonic acid amides of sucrose β-amino-alkyl ethers are further suitable examples and can be synthesized according to methods disclosed in, e.g., Austrian Patent 382,381 (1987), *Chem Abstr* 108:114719, 1988, and Gruber and Greber "Reactive Sucrose Derivatives," in *Carbohydrates as Organic Raw Materials,* Lichtenthaler, ed., VCH Publishers, New York, pp. 95-116, 1991. Derivatives of palatinose or isomaltamine linked by an amide linkage to an alkyl chain and derivatives of isomaltamine linked by urea to an alkyl chain are also suitable and can be synthesized according to methods disclosed in, e.g., Kunz, "Sucrose-based Hydrophilic Building Blocks as Intermediates for the Synthesis of Surfactants and Polymers" in *Carbohydrates as Organic Raw Materials,* Lichtenthaler, ed., VCH Publishers, New York, pp. 127-153, 1991). Long chain aliphatic carbonic acid ureides of sucrose β-amino-alkyl ethers and long chain aliphatic carbonic acid amides of sucrose β-amino-alkyl ethers are also suitable examples and can be synthesized according to methods disclosed in, e.g., Austrian Patent 382,381 (1987), *Chem Abstr* 108:114719, 1988, and Gruber and Greber, "Reactive Sucrose Derivatives" in *Carbohydrates as Organic Raw Materials,* Lichtenthaler, ed., VCH Publishers, New York, pp. 95-116, 1991. The refernces disclosed in this paragraph are each incorporated by reference herein at least for their teachings of the synthesis of alkyl glycosides.

In further examples, the alkyl glycoside can be maltose, sucrose, glucose, or a combination thereof linked by a glycosidic linkage to an alkyl chain of 9, 10, 12 or 14 carbon atoms, e.g., nonyl-, decyl-, dodecyl- and tetradecyl sucroside, glucoside, and maltoside. In these examples, these compositions are nontoxic because they are degraded to an alcohol and an oligosaccharide.

The above aspects are illustrative of the types of the alkyl glycosides that can be used herein and are not exhaustive. Any derivative of the alkyl glycosides described above is contemplated as well.

2. Vaccine

The term "vaccine" as used herein is any agent that induces or potentiates an immunological response in a subject upon administration. In one example, the vaccine can be a protein-based vaccine, a DNA-based vaccine, or a RNA-based vaccine. In other examples, the vaccine can be Antirabies Serum; Antivenin (*Latrodectus mactans*); Antivenin (Micrurus Fulvius); Antivenin (Crotalidae) Polyvalent; BCG Vaccine; Botulism Antitoxin; Cholera Vaccine; Diphtheria Antitoxin; Diphtheria Toxoid; Diphtheria Toxoid Adsorbed; Globulin, Immune; Hepatitis B Immune Globulin; Hepatitis B Virus Vaccine Inactivated; Influenza Virus Vaccine; Measles Virus Vaccine Live; Meningococcal Polysaccharide Vaccine Group A; Meningococcal Polysaccharide Vaccine Group C; Mumps Virus Vaccine Live; Pertussis Immune Globulin; Pertussis Vaccine; Pertussis Vaccine Adsorbed; Plague Vaccine; Poliovirus Vaccine Inactivated; Poliovirus Vaccine Live Oral; Rabies Immune Globulin; Rabies Vaccine; $Rh_o$ (D) Immune Globulin; Rubella Virus Vaccine Live; Smallpox Vaccine; Tetanus Antitoxin; Tetanus Immune Globulin; Tetanus Toxoid; Tetanus Toxoid Adsorbed; Typhoid Vaccine; Yellow Fever vaccine; Vaccinia Immune Globulin; or Varicella-Zoster Immune Globulin.

In many examples disclosed herein, the vaccine is a vector. As used herein, a "vector" is a tool that allows or facilitates the transfer of an entity from one environment to another. In one example, the techniques and products described in U.S. Pat. No. 5,990,091, International Publication Nos. WO 99/60164 and WO98/00166, van Ginkel et al., "Adenoviral gene delivery elicits distinct pulmonary-associated T helper cell responses to the vector and to its transgene," *J Immunol* 159(2):685-93, 1997; and Osterhaus et al, "Vaccination against acute respiratory virus infections and measles in man," *Immunobiology* 184(2-3):180-92, 1992, which contain information concerning expressed gene products, antibodies and uses thereof, vectors for in vivo and in vitro expression of exogenous nucleic acid molecules, promoters for driving expression or for operatively linking to nucleic acid molecules to be expressed, method and documents for producing such vectors, compositions comprising such vectors or nucleic acid molecules or antibodies, dosages, and modes and/or routes of administration (including compositions for nasal administration), inter alia, can be employed in the practice of this invention and are incorporated by herein reference in their entireties.

In other examples, vector compositions are formulated by admixing the vector with a suitable carrier or diluent. In another example, the gene product, the immunological product, or the antibody compositions can be formulated by admixing the gene, the immunological product, or the antibody with a suitable carrier or diluent; see, e.g., U.S. Pat. No. 5,990,091, International Publication Nos. WO 99/60164 and WO 98/00166, and documents cited therein.

In some examples, the vector expresses a gene which encodes, for example, influenza hemaglutinin, influenza nuclear protein, influenza M2, tetanus toxin C-fragment, anthrax protective antigen, anthrax lethal factor, rabies glycoprotein, HBV surface antigen, HIV gp 120, HW gp 160, human carcinoembryonic antigen, malaria CSP, malaria SSP, malaria MSP, malaria pfg, mycobacterium tuberculosis HSP or a mutant thereof. In still other examples, the immune response in the subject is induced by genetic vectors expressing genes encoding antigens of interest in the subject's cells such as, for example, epidermal or mucosal cells. In further examples, the antigen of interest includes, but is not limited to, influenza hemaglutinin, influenza nuclear protein, influenza M2, tetanus toxin C-fragment, anthrax protective antigen, anthrax lethal factor, anthrax germination and outgrowth-associated proteins, rabies glycoprotein, HBV surface antigen, HIV gp 120, HIV gp 160, human carcinoembryonic antigen, malaria CSP, malaria SSP, malaria MSP, malaria pfg, and mycobacterium tuberculosis HSP. In yet other examples, the immune response is against a pathogen or a neoplasm. In other examples, the genetic vector is used as a prophylactic vaccine or a therapeutic vaccine. In still other examples, the genetic vector includes genetic vectors capable of expressing an antigen of interest in the subject's cells.

In the disclosed compositions and methods, the vector can be exogenous DNA. With respect to exogenous DNA for expression in a vector (e.g., encoding an epitope of interest, an antigen, or a therapeutic), U.S. Pat. No. 5,990,091, and International Publication Nos. WO 98/00166 and WO 99/60164, and the documents cited therein, and documents disclose exogenous DNA, as well as the expression of transcription and/or translation factors for enhancing expression of nucleic acid molecules. Any of the exogenous nucleic acid molecules, promoters, and vectors cited in these documents can be in the compositions and methods disclosed herein. Further examples of exogenous nucleic acids that can be used are disclosed in U.S. Pat. Nos. 6,004,777; 5,997,878; 5,989, 561; 5,976,552; 5,972,597; 5,858,368; 5,863,542; 5,833,975; 5,863,542; 5,843,456; 5,766,598; 5,766,597; 5,762,939; 5,756,102; 5,756,101; and 5,494,807, which are each incorporated by reference herein at least for their teachings of exogenous nucleic acids.

In many examples, the vector can be a viral vector, a bacterial vector, a protozoan vector, a retrotransposon, a transposon, a virus shell, or a DNA vector. In another aspect, the viral vector, the bacterial vector, the protozoan vector and the DNA vector can be recombinant vectors. In some examples, the immune response is against influenza A. In other examples, the immune response against influenza A is induced by the genetic vector expressing a gene encoding an influenza hemaglutinin, an influenza nuclear protein, an influenza M2, or a fragment thereof in the subject's cells. In another aspect, the vector can be a viral vector and plasmid DNA.

In another example, the vector can be an adenovirus. In one example, the adenovirus recombinant can include E1-defective, E3-defective, and/or E4-defective adenovirus vectors, or the "gutless" adenovirus vector, where all viral genes are deleted. The "gutless" adenovirus vector is the latest model in the adenovirus vector family. Its replication requires a helper virus and a special human 293 cell line expressing both E1a and Cre, a condition that does not exist in natural environment. The vector is deprived of all viral genes; thus, the vector as a vaccine carrier is non-immunogenic and may be inoculated for multiple times for re-vaccination. The "gutless" adenovirus vector also contains 36 kb space for accommodating transgenes, thus allowing co-delivery of a large number of antigen genes into cells. Specific sequence motifs such as the RGD motif can be inserted into the H-I loop of an adenovirus vector to enhance its infectivity. An adenovirus recombinant is constructed by cloning specific transgenes or fragments of transgenes into any of the adenovirus vectors such as those described above. In one example, the adenovirus recombinant can be used to transduce epidermal or mucosal cells of a subject in a noninvasive mode for use as an immunizing agent. In one example, the adenovirus vector can be defective in its E1 region. In another example, the adenovirus vector can be defective in its E3 region. In a further example, the adenovirus vector can be defective in its E1 and E3 regions. In another example, the DNA is in plasmid form.

Also disclosed herein, the genetic vector can encode an immunomodulatory gene such as, for example, a co-stimulatory gene, a cytokine gene, or a chemokine. In this aspect, the gene can be a GM-CSF gene, a B7-1 gene, a B7-2 gene, an interleukin-2 gene, an interleukin-12 gene and interferon genes.

In other examples, the vector can encode a complete gene, a fragment of a gene or several genes, or gene fragments fused with immune modulatory sequences such as, for example, ubiquitin or CpG-rich synthetic DNA, together with transcription/translation signals necessary for expression.

In other examples, the vector has all viral genes deleted.

In still other examples, the vector induces an anti-tumor effect in the subject. In a further example, the vector expresses an oncogene, a tumor-suppressor gene, or a tumor-associated gene. In another example, the vector further contains a gene such as, for example, a co-stimulatory gene and cytokine gene.

Also disclosed herein, when the vector is a DNA/adenovirus complex, the plasmid DNA can be complexed with adenovirus vectors utilizing a suitable agent such as, for example, polyethylenimine or polylysine. In this aspect, the adenovirus vector within the complex can be either "live" or "killed" by UV irradiation. The UV-inactivated adenovirus vector can be used as a receptor-binding ligand and an endosomolysis agent for facilitating DNA-mediated transfection. In one example, the DNA/adenovirus complex can be used to transfect epidermal or mucosal cells of a subject in a noninvasive mode for use as an immunizing agent.

In other examples, DNA/liposome complexes can be used as the vector to transfect epidermal or mucosal cells of a subject in a noninvasive mode for use as an immunizing agent.

In still other examples, the vector can code for immunomodulatory molecules that can act as an adjuvant to provoke a humoral and/or cellular immune response. Such molecules include, but are not limited to, cytokines, co-stimulatory molecules, or any molecules that may change the course of an immune response.

The vaccines used herein can take any number of forms, and are not limited to any particular genetic material coding for any particular polypeptide. All forms of vectors including viral vectors, bacterial vectors, protozoan vectors, transposons, retrotransposons, virus-like-particles, and DNA vectors, when used as noninvasive vaccine carriers, are contemplated herein.

3. Pharmaceutical Compositions

Also disclosed herein, any of the alkyl glycosides and vaccines described above can be combined with at least one pharmaceutically-acceptable carrier to produce a pharmaceutical composition. In many examples, the pharmaceutical composition comprises an alkyl glycoside and a vector. The pharmaceutical compositions can be prepared using techniques known in the art. In one example, the composition is prepared by admixing the alkyl glycoside and/or vaccine with a pharmaceutically-acceptable carrier. The term "admixing" is defined as mixing the two components together. Depending upon the components to be admixed, there may or may not be a chemical or physical interaction between two or more components.

Pharmaceutically-acceptable carriers are known to those skilled in the art. These most typically would be standard carriers for administration to humans, including solutions such as sterile water, saline, and buffered solutions at physiological pH.

Molecules intended for pharmaceutical delivery may be formulated in a pharmaceutical composition. Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

Preparations for administration include sterile aqueous or non-aqueous solutions, suspensions, and emulsions. Examples of aqueous carriers include water, alcoholic/aqueous solutions, emulsions or suspensions, including saline and buffered media. Parenteral vehicles, if needed for collateral use of the disclosed compositions and methods, include sodium chloride solution. Ringer's dextrose, dextrose and sodium chloride, lactated Ringer's, or fixed oils. Intravenous vehicles, if needed for collateral use of the disclosed compositions and methods, include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, ointments, suppositories, sprays (e.g., aerosols), liquids and powders. Conventional pharmaceutical carriers, aqueous, powder or oily bases, thickeners and the like may be necessary or desirable. The alkyl glycoside and vaccine can be admixed under sterile conditions with a physiologically acceptable carrier and any preservatives, buffers, propellants, or absorption enhancers as may be required or desired. Reference is made to documents cited herein, e.g., U.S. Pat. No. 5,990,091, International Publication Nos. WO 98/00166 and WO 99/60164, for the preparation of compositions for topical applications, e.g., viscous compositions that can be creams or ointments, as well as compositions for nasal and mucosal administration.

In the case when the composition is administered mucosally, ocularly, intranasally, or by inhalation, the formulation can be in the form of a drop, a spray, an aerosol, or a sustained release format. The spray and the aerosol can be achieved through use of the appropriate dispenser. The sustained release format can be an ocular insert, erodible microparticulates, swelling mucoadhesive particulates, pH sensitive microparticulates, nanoparticles/latex systems, ion-exchange resins and other polymeric gels and implants (e.g., Ocusert, which is available from Alza Corp. (Mountain View, Calif.) and those disclosed in International Publication No. WO 91/19481). These systems maintain prolonged drug contact with the absorptive surface preventing washout and nonproductive drug loss.

It will be appreciated that the actual preferred amounts of alkyl glycoside and vaccine in a specified case will vary according to the specific compounds being utilized, the particular compositions formulated, the mode of application, and the particular situs and subject being treated. Dosages for a given host can be determined using conventional considerations, e.g., by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physicians Desk Reference, Barnhart Publishing, 1999.

B. Methods of Use

The methods described herein are useful in the noninvasive immunization of a subject. The term "noninvasive" as used herein is defined as any technique that does not involve the penetration of the tissue of the subject with a device in order to deliver the vaccine. The term "noninvasive," however, does include any pretreatment of the subject prior to administration of the alkyl glycoside and vaccine to the subject. For example, the skin of a subject can be brushed with an abrasive (e.g., a pad or brush) to make the skin more permeable to the alkyl glycoside and vaccine. In one example, described herein is a method for increasing the penetration of a vaccine through the skin of a subject, comprising:
(a) contacting the skin of the subject with an effective amount of an alkyl glycoside; and
(b) contacting the skin of the subject with an effective amount of the vaccine, whereby the amount of vaccine that penetrates the skin of the subject is greater after step (b) when compared to the amount of vaccine that penetrates the skin in the absence of step (a).

In another example, described herein is a method for enhancing an immune response in a subject, comprising:

(a) contacting the skin of the subject with an effective amount of an alkyl glycoside; and
(b) contacting the skin of the subject with an effective amount of a vaccine whereby the immune response is greater after step (b) when compared to the immune response in the absence of step (a).

In a further example, described herein is a method for inducing or potentiating a therapeutic response in a subject, comprising:

(a) contacting the skin of a subject with an effective amount of an alkyl glycoside; and
(b) contacting the skin of the subject an effective amount of a vaccine, thereby inducing or potentiating the therapeutic response in the subject.

In another example, described herein is a method for inducing or potentiating an immune response or a therapeutic response in a subject, comprising:

(a) contacting skin cells of the subject with an effective amount of an alkyl glycoside; and
(b) contacting the skin cells of the subject with an effective amount of a vaccine.

In a further example, described herein is a method a method for increasing the penetration of a vaccine through a mucosal surface of a subject, comprising:

(a) contacting the mucosal surface of the subject with an effective amount of an alkyl glycoside; and
(b) contacting the mucosal surface of the subject with an effective amount of the vaccine, whereby the amount of vaccine that penetrates the mucosal surface of the subject is greater after step (b) when compared to the amount of vaccine that penetrates the mucosal surface in the absence of step (a), wherein the contacting steps (a) and (b) are not performed by inhalation.

In another example, described herein is a method for enhancing an immune response in a subject, comprising:

(a) contacting the mucosal surface of the subject with an effective amount of an alkyl glycoside; and
(b) contacting the mucosal surface of the subject with an effective amount of a vaccine, whereby the immune response is greater after step (b) when compared to the systemic immune response in the absence of step (a), and wherein the contacting steps (a) and (b) are not performed by inhalation.

In a further example, described herein is a method for inducing or potentiating a therapeutic response in a subject, comprising:

(a) contacting the mucosal surface of a subject with an effective amount of an alkyl glycoside; and
(b) contacting the mucosal surface of the subject an effective amount of a vaccine, thereby inducing or potentiating the therapeutic response in the subject, and wherein the contacting steps (a) and (b) are not performed by inhalation.

In another example, described herein is a method for inducing or potentiating an immune response or a therapeutic response in a subject, comprising (a) contacting mucosal cells of the subject with an effective amount of an alkyl glycoside; and
(b) contacting the mucosal cells of the subject with an effective amount of a vaccine, wherein the contacting steps (a) and (b) are not performed by inhalation.

In one example, described herein is a method for increasing the penetration of a vector through the mucosal surface of a subject, comprising:

(a) contacting the mucosal surface of the subject with an effective amount of an alkyl glycoside; and
(b) contacting the mucosal surface of the subject with an effective amount of the vector, whereby the amount of vector that is penetrates the mucosal surface is greater after step (b) when compared to the amount of vector that is absorbed in the absence of step (a).

In another example, described herein is a method for enhancing an immune response in a subject, comprising:
(a) contacting the mucosal surface of the subject with an effective amount of an alkyl glycoside; and
(b) contacting the mucosal surface of the subject with an effective amount of a vector, whereby the immune response is greater after step (b) when compared to the systemic immune response in the absence of step (a).

In a further example, described herein is a method for inducing or potentiating a therapeutic response in a subject, comprising:
(a) contacting the mucosal surface of a subject with an effective amount of an alkyl glycoside; and
(b) contacting the mucosal surface of the subject with an effective amount of a vector, thereby inducing or potentiating the therapeutic response in the subject.

In various aspects, the methods described herein can induce or potentiate an immune response in a subject (e.g., systemic or local immune response) or therapeutic response (e.g., systemic or local therapeutic response). By "induce" means initiating a desired response or result that was not present prior to the induction step. The term "potentiate" means sustaining a desired response at the same level prior to the potentiating step or increasing the desired response over a period of time. The term "enhance" includes both inducing and potentiating a desired response. By "subject" is meant an individual. The subject can include any vertebrate. The subject can be a mammal such as a primate or a human. The term "subject" can also include domesticated animals including, but not limited to, cats, dogs, etc., livestock (e.g., cattle, horses, pigs, sheep, goats, etc.), and laboratory animals (e.g., mouse, rabbit, rat, guinea pig, etc.). The subject can also include birds (e.g., chickens, ducks, or turkeys), reptiles, amphibian, or fish.

The administration of the alkyl glycoside to the subject enhances or increases the desired effect the vaccine can impart (e.g., immunization of the subject) when compared to administering the vaccine in the absence of the alkyl glycoside. With respect to an immune response, one can determine a resulting immune response by any of several methods, including detecting the presence of antibodies specific for the antigen, determining T-cell proliferative response, determining a cytotoxic T-cell response, among other detection means known in the art. Such methods are known in the art and described herein. By "immune response" is meant any response of the immune system, including but not limited to cellular as well as local and systemic humoral immunity, such as CTL responses, including antigen-specific induction of CD8+ CTLs, helper T-cell responses including T-cell proliferative responses and cytokine release, and B-cell responses including antibody response. By "therapuetic response" is meant as the prevention or alleviation of a disease or symptoms of disease due to administration of a vaccine. For example the flu vaccine either prevents a subject from influenza infection or in the case of infection attenuates the infection and consequent symptoms. In another example, a rabies vaccine administered after transmission of virus prevents progression of disease.

In one example, the use of the alkyl glycoside in combination with a vaccine such as, for example, a vector, can increase the penetration (i.e., absorption) of the vaccine into skin or mucosal surface two times, three times, four times, five times, six times, seven times, eight times, nine times, or ten times more when compared to administration of the vaccine in the absence of the alkyl glycoside. Similarly, the alkyl glycoside can increase the immunization or therapeutic effect two times, three times, four times, five times, six times, seven times, eight times, nine times, or ten times more when compared to administration of the vaccine in the absence of the alkyl glycoside.

The alkyl glycoside and vaccine can be administered to a subject sequentially or concurrently. Thus, in one example, the alkyl glycoside can be administered to the subject first followed the administration of the vaccine. In this example, the alkyl glycoside and vaccine can be administered in the same or different media. In another example, the alkyl glycoside and vaccine can be admixed to form a composition, followed by administration of the composition to the subject.

The alkyl glycoside and the vaccine can be administered to the subject in a number of ways depending on whether local or systemic treatment is desired, and on the area to be treated. In one example, administration can be topical, including ophthalmically, vaginally, rectally, or intranasally. In another example, the mode of administration can be by inhalation. In general, the mode of administration does not involve the use of needles or syringes. In one example, the alkyl glycoside and the vaccine are administered in the form of a drop, a spray, an aerosol, a sustained-release format, or a combination thereof.

In another example, the administration step further comprises disposing the vaccine such as, for example, a genetic vector containing the gene of interest on a delivery device and applying the device having the genetic vector containing the gene of interest therein to the skin of the subject.

In another example, the alkyl glycoside and the vaccine are administered to the subject by applying the alkyl glycoside and vaccine to the skin of the subject. In this example, the alkyl glycoside and the vaccine can be administered to the subject by direct transfer of the genetic material to the skin without utilizing any devices, or by contacting naked skin utilizing a bandage or a bandage-like device. In one example, the alkyl glycoside and vaccine are in aqueous solution. Not wishing to be bound by theory, it is believed that the alkyl glycoside makes the skin more permeable to the vaccine and facilitates the ability of the vaccine to pass through the stratum corneum of the skin so that the vaccine can more efficiently reach the epidermal and dermal layers.

In another example, any cell of a subject such as, for example, an epidermal or mucosal cell that can be contacted with the alkyl glycoside and vaccine using noninvasive techniques can be used to induce or potentiate an immune or therapeutic response. By "contacting" is meant an instance of exposure by close physical contact of at least one substance to another substance. For example, contacting can include contacting a substance, such as a pharmacologic agent, with a cell. A cell can be contacted with a test compound, for example, an alkyl glycoside and vaccine, by adding the agent to the culture medium (by continuous infusion, by bolus delivery, or by changing the medium to a medium that contains the agent) or by adding the agent to the extracellular fluid in vivo (by local delivery, systemic delivery, intravenous injection, bolus delivery, or continuous infusion). Alternatively, the contacting step can be performed in vitro or ex vivo. The duration of contact with a cell or group of cells is determined by the time the test compound is present at physiologically effective levels or at presumed physiologically effective levels in the medium or extracellular fluid bathing the cell.

The methods described herein contemplate the use of one or more alkyl glycosides and vaccines. For example, two or more vaccines can be admixed with one or more alkyl glycosides to produce a composition to be administered to a subject. In another example, one or more alkyl glycosides can be administered first followed by the administration of two or more different vaccines. The noninvasive methods described herein can also be used in combination with other therapies that utilize invasive techniques. Thus, in one example, a vaccine can be administered to a subject using invasive techniques prior to or after the noninvasive administration of alkyl glycoside and vaccine. The methods described herein also contemplate periodic administration of the alkyl glycoside and vaccine such as in the course of therapy or treatment for a condition and/or booster administration of immunological compositions and/or in prime-boost regimens, where the time and manner for sequential administrations can be ascertained without undue experimentation.

As described above, the quantity of alkyl glycoside and vaccine to be administered will vary depending upon the alkyl glycoside and vector selected, the mode of administration, and the subject. By "effective amount" is meant a therapeutic amount needed to achieve the desired result or results, e.g., increasing the expression of a gene. In one example, the amount of alkyl glycoside is in the range of from about 0.01% to about 10%, from about 0.01% to about 9%, from about 0.01% to about 8%, from about 0.01% to about 7%, from about 0.01% to about 6%, from about 0.01% to about 5%, from about 0.01% to about 4%, from about 0.01% to about 3%, from about 0.01% to about 2%, from about 0.01% to about 1%, from about 0.01% to about 0.9%, from about 0.01% to about 0.8%, from about 0.01% to about 0.7%, from about 0.01% to about 0.6%, from about 0.01% to about 0.5%, from about 0.025% to about 5%, from about 0.05% to about 0.5%, or from about 0.125% to about 0.5% by weight of the composition. In other examples, the amount of vaccine can vary from one or a few to a few hundred or thousand micrograms, e.g., 1 µg to 1 mg, 1 µg to 0.75 mg, 1 µg to 0.5 mg, 1 µg to 0.1 mg. In another example, the amount of vaccine to be administered is from 100 ng/kg to 100 mg/kg, 100 ng/kg to 75 mg/kg, 100 ng/kg to 50 mg/kg, 100 ng/kg to 10 mg/kg of body weight per day. The amount of alkyl glycoside and vaccine to be administered can be readily determined using techniques known in the art.

Also described herein are methods for producing gene products, immunological products, or antibodies in vivo, in vitro, or ex vivo. In one example, a gene product can be isolated from cells from a subject, where the vaccine such as, for example, a vector, was administered to a subject using the compositions and methods described herein. In another example, the immunological products, antibodies, or expressed products obtained by the methods described herein can be expressed in vitro and used in a manner where immunological products, expressed products, or antibodies are typically used. In this example, the cells that express the immunological product, expressed product, or antibody can be employed in vitro and/or ex vivo applications such as, for example, in diagnostics, assays, and ex vivo therapy. U.S. Pat. No. 5,990,091, International Publication Nos. WO 99/60164 and WO 98/00166 disclose the use of cells that express the gene product and/or immunological response, expanded in vitro, and reintroduced into the host or animal. In another example, expressed antibodies or gene products that are produced and isolated from the methods described herein can be administered in compositions in a manner similar to the administration of subunit epitopes, antigens, therapeutics, or antibodies to induce or potentiate an immune or therapeutic response.

C. Devices and Kits

Described herein are delivery devices that contain any of the compositions described above and claimed herein. In one example, the delivery device can be a bandage, a patch, an adhesive dressing, a spot-on formulation and its application devices, a pour-on formulation and its application devices, a roll-on formulation and its application devices, a shampoo formulation and its application devices, and the like. Pour-on and spot-on formulations are described in U.S. Pat. Nos. 6,010,710 and 5,475,005. A roll-on device is described in U.S. Pat. No. 5,897,267. The contents of these documents are hereby incorporated by reference for their teachings.

In one example, the device is an adhesive bandage. Referring to FIG. 1, a device for non-invasive vaccination is shown. This vaccine delivery device includes a non-allergenic, skin adhesive patch having a bleb disposed therein. In one example, the patch is further composed of plastic, approximately 1 cm in diameter. The vaccine composition can be disposed within the bleb. In another example, the bleb contains approximately 1 mL of vaccine (as liquid, lyophilized powder with reconstituting fluid, and variants thereof). In another example, the surface of the bleb in contact with the skin is intentionally weaker than the opposite surface, such that when pressure is applied to the opposite surface, the lower surface breaks and releases the vaccine contents of the bleb onto the skin. The plastic patch traps the vaccine against the skin surface. In this example, the alkyl glycoside can be applied to the skin followed by the application of the patch or, in the alternative, the patch can contain the alkyl glycoside and the vaccine.

Also described herein are kits for the preparation of compositions for the noninvasive delivery of vaccines. The kit includes the alkyl glycoside, the vaccine and an optional pharmaceutically-acceptable carrier or diluent. The components can be in separate containers each in its own packaging, and the kit can optionally include instructions for admixture of the ingredients and/or administration of the composition. The kit can also optionally contain a delivery device.

EXAMPLES

The following examples are put forth so as to provide those of ordinary skill in the art with a complete disclosure and description of how the compounds, compositions, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Preliminary tests of the ability of tetradecyl-β-D maltoside (purchased from Anatrace) to enhance the potency of an *E. coli*-vectored epicutaneous vaccine when co-administered without ablation of the stratum corneum were conducted.

Specifically, mice were immunized by topical application of an *E. coli* vector expressing tetC mixed with TDM at the indicated concentration and sera were analyzed 2 months postimmunization. No increase over the control was observed when the skin was not ablated by brushing.

Tests of the ability of TDM to enhance the potency of an adenovirus-vectored epicutaneous vaccine when co-administered without ablation of the stratum corneum were also conducted. Here, mice were immunized by topical application of an adenovirus vector expressing tetC mixed with TDM at the indicated concentration, and sera were analyzed 1 month postimmunization. No significant increase over the control was observed.

Figure 2:
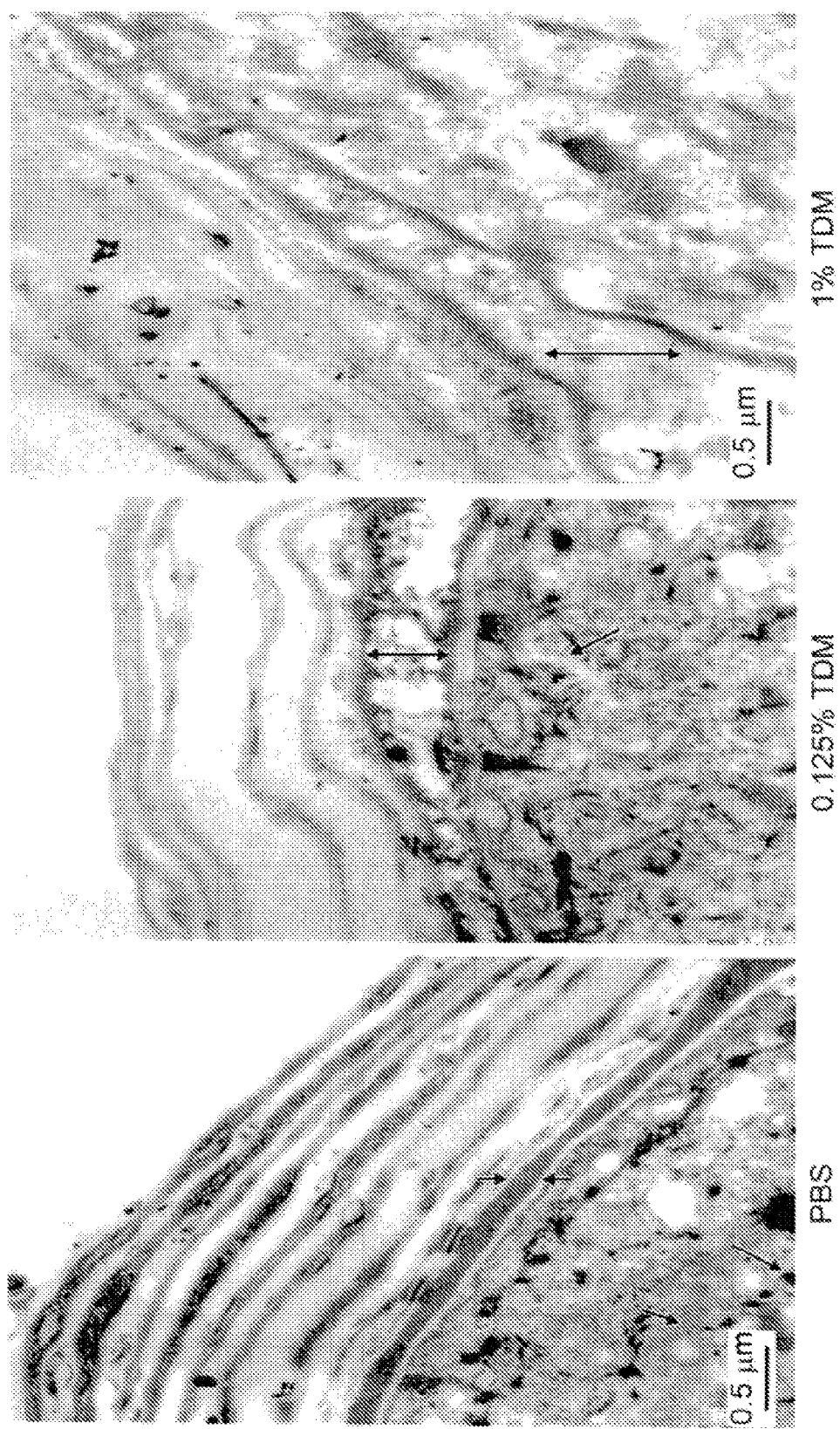
FIG. 2 shows the permeablization of stratum corneum by tetradecyl-β-D-maltoside surfactant.
Figure 3:
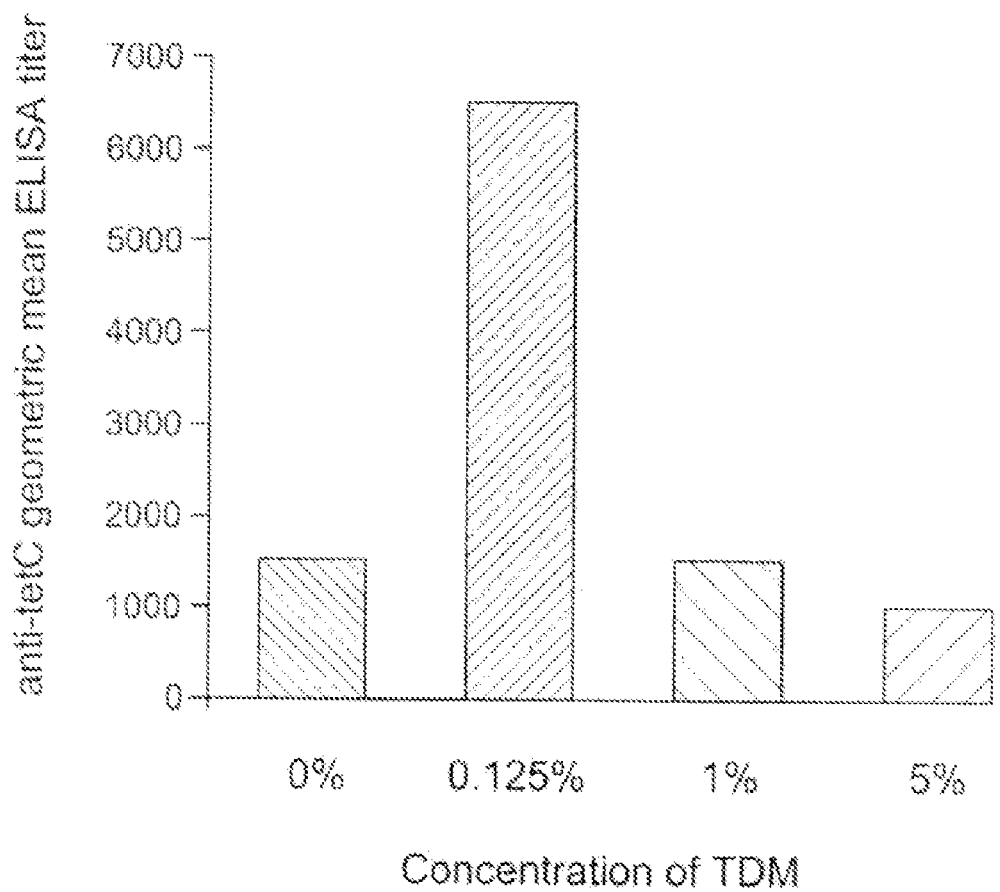
FIG. 3 shows the effect of tetradecyl-β-D-maltoside (TDM) as an epicutaneous vaccine enhancer.

Mouse skin was ablated by mechanical brushing prior to topical application of TDM, followed by incubation of TDM at the indicated concentration with naked skin for 15 min, followed by examination of the cutaneous architecture under an electron microscope. FIG. 2 shows the permeablization of the stratum comeum by the TDM surfactant.

Tests of the ability of TDM to enhance the potency of an *E. coli*-vectored epicutaneous vaccine when co-administered with ablation of the stratum corneum were also conducted. Here, mouse skin was ablated by mechanical brushing prior to topical application of TDM at the indicated concentration. After incubation for 15 min, TDM was removed and mice were immunized by topical application of an *E. coli* vector expressing tetC, and sera were analyzed 2 weeks postimmunization. The results are shown in FIG. 3.

Throughout this application, various publications are referenced. The disclosures of these publications in their entireties are hereby incorporated by reference into this application in order to more fully describe the compounds, compositions and methods described herein.

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A method for increasing the penetration of a vaccine through the skin of a subject, comprising: (a) contacting the skin of the subject with a first composition comprising an effective amount of an alkyl glycoside, wherein the first composition is free of oil; and (b) contacting the skin of the subject with a second composition comprising an effective amount of the vaccine, wherein the second composition is free of oil, whereby the amount of vaccine that penetrates the skin of the subject is greater after step (b) when compared to the amount of vaccine that is absorbed in the absence of step (a).

2. The method of claim 1, wherein the alkyl glycoside is nonionic.

3. The method of claim 1, wherein the alkyl group comprises from 6 to 24 carbons.

4. The method of claim 1, wherein the alkyl group comprises from 6 to 14 carbon atoms.

5. The method of claim 1, wherein the saccharide comprises erythrose, threose, ribose, arabinose, xylose, lyxose, allose, altrose, glucose, mannose, gulose, idose, galactose, talose, fructose, maltose, cellobiose, maltotriose, maltotetraose, sucrose, lactose, trehalose, raffinose, or a derivative or combination thereof.

6. The method of claim 1, wherein the linkage comprises a glycosidic linkage, a thioglycosidic linkage, an amide linkage, a ureide linkage, an ester linkage, or a combination thereof.

7. The method of claim 1, wherein the alkyl glycoside comprises a hydrophile-lipophile balance number in the range of about 10 to 20.

8. The method of claim 1, wherein the alkyl glycoside comprises an alkyl thiomaltoside, an alkyl thioglucoside, or an alkyl thiosucrose.

9. The method of claim 1, wherein the alkyl glycoside comprises hexyl-, heptyl-, octyl-, nonyl-, decyl-, undecyl-, dodecyl-, tridecyl-, tetradecyl-, pentadecyl-, hexadecyl-, heptadecyl-, or octadecyl α- or β-D-maltoside; hexyl-, heptyl-, octyl-, nonyl-, decyl-, undecyl-, dodecyl-, tridecyl-, tetradecyl-, pentadecyl-, hexadecyl-, heptadecyl-, or octadecyl α- or β-D-glucoside; hexyl-, heptyl-, octyl-, nonyl-, decyl-, undecyl-, dodecyl-, tridecyl-, tetradecyl-, pentadecyl-, hexadecyl-, heptadecyl-, or octadecyl esters of sucrose; hexyl-, heptyl-, octyl-, dodecyl-, tridecyl-, or tetradecyl-β-D-thiomaltoside; heptyl- or octyl-1-thio-β-glucopyranoside; heptyl- or octyl-1-thio-β-D-glucopyranoside; a long chain aliphatic carbonic acid amide of a sucrose β-amino-alkyl ether; a derivative of palatinose or isomaltamine linked by an amide linkage to an alkyl chain; a derivative of isomaltamine linked by urea to an alkyl chain, a long chain aliphatic carbonic acid ureide of a sucrose β-amino-alkyl ether; or a long chain aliphatic carbonic acid amide of a sucrose β-amino-alkyl ether.

10. The method of claim 1, wherein the alkyl glycoside comprises a saccharide comprising maltose, sucrose, glucose, or a combination thereof linked to an alkyl group having from 6 to 14 carbon atoms by a glycosidic linkage.

11. The method of claim 1, wherein the alkyl glycoside has a concentration in the range of about 0.01% to 10%.

12. The method of claim 1, wherein the vaccine comprises a vectored-vaccine, a protein-based vaccine, a DNA-based vaccine, or a RNA-based vaccine.

13. The method of claim 1, wherein the vaccine comprises a vector.

14. The method of claim 13, wherein the vector comprises a viral vector.

15. The method of claim 13, wherein the vector comprises a bacterial vector.

16. The method of claim 13, wherein the vector comprises an *E. coli* vector.

17. The method of claim 13, wherein the vector comprises and expresses a nucleic acid molecule encoding a gene product.

18. The method of claim 17, wherein the nucleic acid molecule encodes an antigen.

19. The method of claim 17, wherein the nucleic acid molecule encodes one or more of: influenza hemaglutinin, influenza nuclear protein, influenza M2, tetanus toxin C-fragment, anthrax protective antigen, anthrax lethal factor, anthrax germination and outgrowth-associated protein, rabies glycoprotein, HBV surface antigen, HIV gp 120, HIV gp 160, human carcinoembryonic antigen, malaria CSP, malaria SSP, malaria MSP and malaria pfg.

20. The method of claim 17, wherein the nucleic acid molecule is exogenous or heterologous to the vector.

21. The method of claim 20, wherein the exogenous or heterologous nucleic acid molecule encodes an epitope.

22. The method of claim 20, wherein the exogenous or heterologous nucleic acid molecule encodes one or more antigens or a portion thereof from a pathogen of the subject or one or more epitopes from a pathogen of the subject.

23. The method of claim 20, wherein the exogenous or heterologous nucleic acid molecule encodes an immunomodulatory gene or a therapeutic gene.

24. The method of claim 23, wherein the immunomodulatory gene comprises a co-stimulator, a cytokine, a chemokines, or a combination thereof.

25. The method of claim 1, wherein the vaccine comprises a nucleic acid molecule that encodes a gene product that stimulates and/or modulates an immunological response.

26. The method of claim 1, wherein the vaccine comprises a nucleic acid molecule that translates an endogenous and/or exogenous nucleic acid molecule.

27. The method of claim 1, wherein the vaccine induces a systemic immune response against a pathogen or a neoplasm.

28. The method of claim 1, wherein the vaccine comprises a DNA/liposome complex.

29. The method of claim 1, wherein the vaccine is matched to or is a natural pathogen of the subject.

30. The method of claim 1, wherein the subject comprises a human.

31. The method of claim 1, wherein the alkyl glycoside and the vaccine are administered non-invasively.

32. The method of claim 1, wherein the alkyl glycoside and the vaccine are administered to the subject in the form of a patch, an ointment, a cream, a lotion, a drop, a spray, an aerosol, a sustained-release format, or a combination thereof.

33. The method of claim 1, wherein the alkyl glycoside and the vaccine are administered to the subject topically.

34. The method of claim 33, wherein upon topical administration to the subject, the vaccine penetrates the stratum corneum of the subject and reaches the dermal and epidermal layers of the subject.

35. The method of claim 1, wherein the alkyl glycoside and the vaccine are administered sequentially to the subject.

36. The method of claim 1, wherein the alkyl glycoside and the vaccine are administered concurrently to the subject.

37. The method of claim 1, wherein a second vaccine is administered invasively prior to step (a) and/or after step (b).

38. The method of claim 1, wherein prior to step (a), brushing the skin with an abrasive.

39. A method for enhancing, inducing, or potentiating an immune response or a therapeutic response in a subject, comprising: (a) contacting skin cells of the subject with a first composition comprising an effective amount of an alkyl glycoside, wherein the first composition is free of oil; and (b) contacting the skin cells of the subject with a second composition comprising an effective amount of a vaccine, wherein the second composition is free of oil.

40. The method of claim 39, wherein the immune response is greater after step (b) when compared to the immune response in the absence of step (a), thereby resulting in an enhanced immune response in a subject.

41. The method of claim 40, wherein the immune response is a systemic immune response.

42. The method of claim 39, wherein the contacting step is in vivo.

* * * * *

UNITED STATES PATENT AND TRADEMARK OFFICE
CERTIFICATE OF CORRECTION

| | |
|---|---|
| PATENT NO. | : 7,524,510 B2 |
| APPLICATION NO. | : 11/360761 |
| DATED | : April 28, 2009 |
| INVENTOR(S) | : John Jefferson Arnold et al. |

It is certified that error appears in the above-identified patent and that said Letters Patent is hereby corrected as shown below:

In Claim 9, Line 22, please delete "chain," and insert --chain;--.

Signed and Sealed this

Fourth Day of August, 2009

JOHN DOLL
*Acting Director of the United States Patent and Trademark Office*

UNITED STATES PATENT AND TRADEMARK OFFICE
CERTIFICATE OF CORRECTION

| | |
|---|---|
| PATENT NO. | : 7,524,510 B2 |
| APPLICATION NO. | : 11/360761 |
| DATED | : April 28, 2009 |
| INVENTOR(S) | : John Jefferson Arnold et al. |

It is certified that error appears in the above-identified patent and that said Letters Patent is hereby corrected as shown below:

Column 18, In Claim 9, Line 22, please delete "chain," and insert --chain;--.

This certificate supersedes the Certificate of Correction issued August 4, 2009.

Signed and Sealed this

First Day of September, 2009

David J. Kappos
*Director of the United States Patent and Trademark Office*